US011891496B2

(12) United States Patent
Hoyer et al.

(10) Patent No.: US 11,891,496 B2
(45) Date of Patent: Feb. 6, 2024

(54) CYANOACRYLATE COMPOSITION WITH HAZARDLESS STABILIZER

(71) Applicant: H.B. Fuller Company, St. Paul, MN (US)

(72) Inventors: Lars P. Hoyer, Seelze (DE); Wolfgang Wittwer, Pirmasens (DE)

(73) Assignee: H.B. Fuller Company, St. Paul, MN (US)

( * ) Notice: Subject to any disclaimer, the term of this patent is extended or adjusted under 35 U.S.C. 154(b) by 34 days.

(21) Appl. No.: 17/653,578

(22) Filed: Mar. 4, 2022

(65) Prior Publication Data
US 2022/0282063 A1 Sep. 8, 2022

Related U.S. Application Data

(60) Provisional application No. 63/157,289, filed on Mar. 5, 2021.

(51) Int. Cl.
  C08F 2/46 (2006.01)
  C08F 2/50 (2006.01)
  C08G 61/04 (2006.01)
  C08K 5/134 (2006.01)
  C08F 120/36 (2006.01)
(52) U.S. Cl.
  CPC ............ C08K 5/134 (2013.01); C08F 120/36 (2013.01)
(58) Field of Classification Search
  CPC . C07C 253/32; C09D 4/00; C09J 4/00; C08K 5/134; C08F 122/32; C08F 120/36; C08F 222/322
  USPC ........................................................ 522/2, 1
  See application file for complete search history.

(56) References Cited

U.S. PATENT DOCUMENTS

| 4,182,823 A | 1/1980 | Schoenberg |
| 4,460,759 A | 7/1984 | Robins |
| 5,530,037 A | 6/1996 | McDonnell et al. |
| 6,607,632 B1 | 8/2003 | McDonnell et al. |
| 8,753,684 B2 | 6/2014 | Pfluecker et al. |
| 10,799,464 B2 | 10/2020 | Anderson et al. |
| 2007/0078207 A1* | 4/2007 | Jonn ..................... C09J 4/00 524/556 |
| 2008/0131381 A1 | 6/2008 | Chaudhuri et al. |
| 2018/0207080 A1 | 7/2018 | Loch et al. |
| 2020/0239618 A1 | 7/2020 | Barnes et al. |
| 2021/0251861 A1 | 8/2021 | Athalin et al. |

FOREIGN PATENT DOCUMENTS

| DE | 102007019043 A1 | 10/2008 |
| WO | WO2010060513 A2 | 9/2010 |
| WO | WO2020085335 A1 | 4/2020 |
| WO | WO2020187773 A1 | 9/2020 |

OTHER PUBLICATIONS

Doudin et al., New genre of antioxidants from renewable natural resources: Synthesis and characterization of rosemary plant-derived antioxidants and their performance in polyolefins, 2016, Polymer Degradation and stability, 130, 126-134 (Year: 2016).*
Merck, "Oxynex® ST Liquid", Brochure 2017.
Merck, "130217 Oxynex® ST Liquid" Technical Data Sheet 2017.
Alexander Kielbassa, Merck, "Up-to-Date Protection Against Light—From UV-IR", PM-PFS Cosmetics Functional, ppt. Jan. 2015.

* cited by examiner

Primary Examiner — Jessica Whiteley
(74) Attorney, Agent, or Firm — Kristi Halloran

(57) ABSTRACT

The present invention relates to a curable cyanoacrylate composition comprising (i) at least one cyanoacrylate monomer, and (ii) at least one free radical stabilizer, wherein the free radical stabilizer is non-hazardous and shows good compatibility to the cyanoacrylate but does not impair the reactivity of the cyanoacrylate and its performance after curing.

17 Claims, No Drawings

CYANOACRYLATE COMPOSITION WITH HAZARDLESS STABILIZER

This application claims the benefit of U.S. Provisional Patent Application No. 63/157,289 filed on Mar. 5, 2021 which is incorporated herein.

FIELD OF THE INVENTION

The present invention relates to a curable cyanoacrylate composition comprising (i) at least one cyanoacrylate monomer, and (ii) at least one free radical stabilizer of the formula (I) as defined below. The free radical stabilizer of formula (I) is non-hazardous and shows good compatibility to the cyanoacrylate but does not impair the reactivity of the cyanoacrylate and its performance after curing. The present invention also relates to the use of a compound of formula (I) for inhibiting free radical polymerization in a composition comprising at least one cyanoacrylate monomer.

BACKGROUND OF THE INVENTION

Cyanoacrylate compositions are well-known in the art. In particular, cyanoacrylates represent a family of strong, fast-setting adhesives with industrial, medical, cosmetic and household uses. Such compositions are sometimes also generically referred to as instant glues, power glues or superglues containing monomers with cyanoacrylate groups. The cyanoacrylate groups in the monomers rapidly polymerizes in the presence of nucleophiles, such as e.g. hydroxide ions generated from water, to form long, strong chains. Details of cyanoacrylate adhesive compositions are summarized e.g. in H. V. Coover, D. W. Dreifus and J. T. O'Connor, "Cyanoacrylate Adhesives" in Handbook of Adhesives, 27, 463-77, I. Skeist, ed., Van Nostrand Reinhold, New York, 3$^{rd}$ ed. (1990); or G. H. Millet, "Cyanoacrylate Adhesives" in Structural Adhesives: Chemistry and Technology, S. R. Hartshorn, ed., Plenum Press, New York, p. 249-307 (1986).

In view of the high reactivity of the cyanoacrylate group, cyanoacrylate compositions have a short shelf-life. As cyanoacrylates can also undergo free radical polymerization, cyanoacrylate adhesives need to be stabilized during storage against free radical destabilization. Stabilizer systems for cyanoacrylates are well-known in the art as disclosed in e.g. WO 2019/068690. For example, hydroquinone (HQ) is the most common for use as a free radical stabilizer in cyanoacrylate compositions. Another typically used free radical stabilizer in cyanoacrylate compositions is e.g. butylated hydroxyanisole (BHA). Other known suitable free radical stabilizers for cyanoacrylate compositions include e.g. Irganox 1010 (CAS No. 6683-19-8) or Irganox 1076 (CAS No. 2082-79-3).

However, HQ is classified e.g. in the EU as a harmful substance (signal word "Danger"), and possibly carcinogenic or mutagenic. Furthermore, BHA is reasonably anticipated e.g. by the U.S. National Institutes of Health to be a human carcinogen, and is listed e.g. by the state of California as a carcinogen. Irganox 1010 is classified as a dangerous good in at least Canada, and several hazards are reported e.g. by the European Chemicals Agency (ECHA). Possible hazards are stated by the ECHA in the case of Irganox 1076 as well. As regards phenol-based antioxidants in general, there are hazards reported for nearly every species. Although some reports are not yet fully proven, other phenol-based antioxidants are stated to be hazardous depending on the world region and the local regulation/legislation. On the other hand, for those species not proven so far as hazardous, there is no known industrial-scale synthesis, which means the demand for cost-efficiency is not given.

Thus, there is a need in the art for alternative free radical stabilizers in cyanoacrylate compositions. In other words, a free radical stabilizer is needed, which, on the one hand, is compatible with cyanoacrylates and is effective to prevent free radical polymerization in cyanoacrylate compositions, and on the other hand, is according to current knowledge non-hazardous and exhibits no health concerns.

However, cyanoacrylates are fast setting adhesives on nearly all materials, which means that they have a high tendency to polymerize once getting into contact with most materials. There are very few chemistries that do not show reactivity towards cyanoacrylates. For example, there are more than 200 different grades of poly(methyl methacrylate) (PMMA) available on the market. However, only very few of them are known to be compatible when diluted in cyanoacrylates as a thickener; all other grades initiate polymerization within minutes to days. As a further example regarding possible packaging materials, there are thousands of polyethylene grades available in the market; however, less than five grades thereof show good compatibility with cyanoacrylates. Thus, in view of the peculiar chemistry and high reactivity involved, it is quite difficult to find compatible materials to work with cyanoacrylates at all, let alone to find compatible materials exerting a specific function such as inhibition of free radical polymerization.

In view of the above, it is an object of the present invention to identify compounds that, on the one hand, are compatible with cyanoacrylates and inhibit free radical polymerization, and on the other hand, are non-hazardous. In particular, it is an object of the present invention to identify free radical stabilizers which are not classified as hazardous, are cost-efficient and show good compatibility with cyanoacrylate formulations.

SUMMARY OF THE INVENTION

The present invention relates to cyanoacrylate compositions comprising non-hazardous free radical stabilizers. In particular, the present invention provides a curable cyanoacrylate composition comprising
(i) at least one cyanoacrylate monomer, and
(ii) at least one free radical stabilizer,
wherein the free radical stabilizer comprises one or more compound(s) of formula (I)

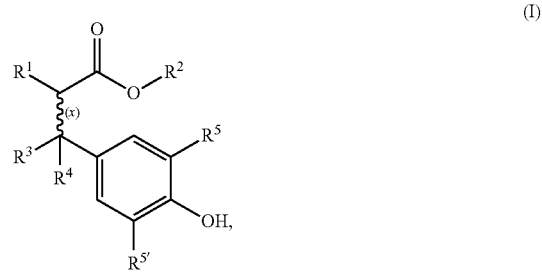

wherein (x) denotes either a double bond and $R^3$ is absent, or (x) denotes a single bond and $R^3$ is hydrogen, linear $C_1$-$C_8$ alkyl, branched or cyclic $C_3$-$C_8$ alkyl, linear $C_1$-$C_8$ alkoxy, branched or cyclic $C_3$-$C_8$ alkoxy, linear $C_2$-$C_8$ alkenyl, or branched or cyclic $C_3$-$C_8$ alkenyl;

$R^1$ is hydrogen, linear $C_1$-$C_8$ alkyl, branched or cyclic $C_3$-$C_8$ alkyl, linear $C_1$-$C_8$ alkoxy, branched or cyclic $C_3$-$C_8$ alkoxy, linear $C_2$-$C_8$ alkenyl, branched or cyclic $C_3$-$C_8$ alkenyl, or a group —C(O)—O—$R^{2'}$, wherein $R^{2'}$ is linear $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl, which linear $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl optionally may be interrupted by one or more oxygen atoms;

$R^2$ is linear $C_1$-$C_{12}$ alkyl, branched or cyclic $C_3$-$C_{12}$ alkyl, linear $C_2$-$C_{12}$ alkenyl, or branched or cyclic $C_3$-$C12$ alkenyl, which linear $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl optionally may be interrupted by one or more oxygen atoms;

$R^4$ is hydrogen, linear $C_1$-$C_8$ alkyl, branched or cyclic $C_3$-$C_8$ alkyl, linear $C_1$-$C_8$ alkoxy, branched or cyclic $C_3$-$C_8$ alkoxy, linear $C_2$-$C_8$ alkenyl, or branched or cyclic $C_3$-$C_8$ alkenyl; and $R^5$ and $R^{5'}$ independently are hydrogen or a group —O—$R^6$, wherein $R^6$ independently is hydrogen, linear $C_1$-$C_8$ alkyl, branched or cyclic $C_3$-$C_8$ alkyl, linear $C_2$-$C_8$ alkenyl, or branched or cyclic $C_3$-$C_8$ alkenyl, wherein one of $R^3$ or $R^4$ together with $R^1$ may form a 5- to 18-membered saturated or unsaturated ring together with the carbon atoms to which they are attached, which is optionally interrupted by one or more oxygen atoms; or $R^3$ and $R^4$ may form a 5- to 18-membered saturated or unsaturated ring together with the carbon atom to which they are attached which is optionally interrupted by one or more oxygen atoms; or $R^1$ with $R^3$ and $R^4$ together with the carbon atoms to which they are attached may form a 5- to 12-membered saturated or unsaturated bicyclic ring, which is optionally interrupted by one or more oxygen atoms.

The present invention further relates to the use of a compound of formula (I) as defined above for inhibiting free radical polymerization in a composition comprising at least one cyanoacrylate monomer.

The present inventor unexpectedly found that conventional free radical stabilizers can be replaced by free radical stabilizers of formula (I), which are presently not classified as hazardous. The non-hazardous free radical stabilizers of formula (I) can well be formulated into cyanoacrylates. Furthermore, the resulting cyanoacrylate compositions achieve similar properties in e.g. shelf-life as well as adhesive properties compared to state-of-art compositions containing hazardous stabilizers such as e.g. hydroquinone (HQ) or butylated hydroxyanisole (BHA).

DETAILED DESCRIPTION OF THE INVENTION

The present invention relates to a curable cyanoacrylate composition comprising (i) at least one cyanoacrylate monomer, and (ii) at least one free radical stabilizer, wherein the free radical stabilizer comprises one or more compound(s) of formula (I)

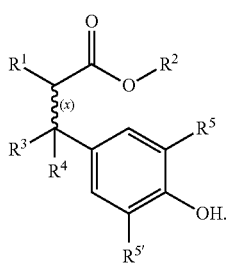

(I)

In the above formula (I), (x) denotes either a double bond or a single bond. In the case of a double bond, $R^3$ is absent. On the other hand, when (x) denotes a single bond, $R^3$ is hydrogen, linear $C_1$-$C_8$ alkyl, branched or cyclic $C_3$-$C_8$ alkyl, linear $C_1$-$C_8$ alkoxy, branched or cyclic $C_3$-$C_8$ alkoxy, linear $C_2$-$C_8$ alkenyl, or branched or cyclic $C_3$-$C_8$ alkenyl. Furthermore, when (x) denotes a single bond, $R^3$ is in preferred embodiments, hydrogen, linear $C_1$-$C_4$ alkyl, or branched $C_3$-$C_4$ alkyl, preferably $R^3$ is hydrogen or methyl, more preferably hydrogen. Alternatively, when (x) is a double bond, $R^3$ is completely absent as noted above.

$R^1$ in the above formula (I) is hydrogen, linear $C_1$-$C_8$ alkyl, branched or cyclic $C_3$-$C_8$ alkyl, linear $C_1$-$C_8$ alkoxy, branched or cyclic $C_3$-$C_8$ alkoxy, linear $C_2$-$C_8$ alkenyl, branched or cyclic $C_3$-$C_8$ alkenyl, or a group —C(O)—O—$R^{2'}$. $R^{2'}$ in the group —C(O)—O—$R^{2'}$ is linear $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl. The $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl in group $R^{2'}$ may optionally be interrupted by one or more oxygen atoms, such as e.g. one or two oxygen atoms.

In preferred embodiments, $R^1$ is a group —C(O)—O—$R^{2'}$. More preferably, $R^1$ is a group —C(O)—O—$R^{2'}$, wherein $R^{2'}$ is branched or cyclic $C_3$-$C_{12}$ alkyl, which is optionally interrupted by one or two oxygen atoms. $R^{2'}$ is preferably branched $C_6$-$C_{10}$ alkyl such as 2-ethylhexyl.

$R^2$ in the above formula (I) is linear $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl. The $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl in group $R^2$ may optionally be interrupted by one or more oxygen atoms, such as e.g. one or two oxygen atoms. In a preferred embodiment, $R^2$ is branched or cyclic $C_3$-$C_{12}$ alkyl, which is optionally interrupted by one or two oxygen atoms. More preferably, $R^2$ is branched $C_6$-$C_{10}$ alkyl such as 2-ethylhexyl.

$R^4$ in the above formula (I) is hydrogen, linear $C_1$-$C_8$ alkyl, branched or cyclic $C_3$-$C_8$ alkyl, linear $C_1$-$C_8$ alkoxy, branched or cyclic $C_3$-$C_8$ alkoxy, linear $C_2$-$C_8$ alkenyl, or branched or cyclic $C_3$-$C_8$ alkenyl. In preferred embodiments, $R^4$ is hydrogen, linear $C_1$-$C_4$ alkyl, or branched $C_3$-$C_4$ alkyl. Preferably, $R^4$ is hydrogen or methyl, more preferably hydrogen.

In addition, one out of $R^3$ or $R^4$ may together with $R^1$ form a 5- to 18-membered saturated or unsaturated ring together with the carbon atoms to which they are attached, which ring optionally may be interrupted by one or more oxygen atoms. For example, one of $R^3$ or $R^4$ may together with $R^1$ form a 5- or 6-membered saturated or unsaturated ring together with the carbon atoms to which they are attached, which ring optionally may be interrupted by one or two oxygen atoms. $R^3$ and $R^4$ together may also form a 5- to 18-membered saturated or unsaturated ring with the carbon atom to which they are attached, which ring may optionally be interrupted by one or more oxygen atoms. For example, $R^3$ and $R^4$ together may form a 5- or 6-membered saturated or unsaturated ring with the carbon atom to which they are attached, which ring optionally may be interrupted by one or two oxygen atoms. Furthermore, $R^1$, $R^3$ and $R^4$ together with the carbon atoms to which they are attached may form a 5- to 12-membered saturated or unsaturated bicyclic ring, which bicyclic ring may be optionally interrupted by one or more oxygen atoms. For example, $R^1$, $R^3$ and $R^4$ together with the carbon atoms to which they are attached may form a 5- to 6-membered saturated or unsaturated bicyclic ring, which bicyclic ring may be optionally interrupted by one or two oxygen atoms.

$R^5$ and $R^{5'}$ in formula (I) are independently of each other hydrogen or a group —O—$R^6$. The $R^6$ in the group —O—$R^6$ independently is hydrogen, linear $C_1$-$C_8$ alkyl, branched or cyclic $C_3$-$C_8$ alkyl, linear $C_2$-$C_8$ alkenyl, or branched or cyclic $C_3$-$C_8$ alkenyl, preferably $R^6$ is independently hydrogen, linear $C_1$-$C_4$ alkyl, or branched $C_3$-$C_4$ alkyl. In preferred embodiments, $R^5$ and $R^{5'}$ independently of each other are hydrogen, —O—$CH_3$ or —$OCH_2CH_3$. Preferably, $R^5$ and $R^{5'}$ are both —O—$CH_3$.

Illustrative compounds found to be compatible with cyanoacrylates in accordance with the present invention having no hazard classification are available on the market and include, for example, diethylhexyl syringylidenemalonate (2-(4-hydroxy-3,5-dimethoxy-benzylidene)-malonic acid bis-(2-ethylhexyl)ester; CAS No. 444811-29-4) marketed by Merck KGaA (Germany) as Oxynex® ST or Oxynex® ST Liquid. Another illustrative commercially available example suitable according to the present invention is bis(2-ethylhexyl)2-[(4-hydroxy-3,5-dimethoxyphenyl)methyl]propanedioate (CAS No. 872182-46-2) marketed by Merck KGaA (Germany) as RonaCare® AP. Other illustrative compounds include but are not limited to diethyl [(4-hydroxy-3-methoxyphenyl)methylidene]propanedioate (CAS No. 24331-83-7), or propanedioic acid,2-[(3,4,5-trimethoxyphenyl)methylene]-,1,3-diethyl ester (CAS No. 51444-50-9).

Compounds in accordance with the above are free of a hazard classification and are described in e.g. WO 2019/229401 for use in cosmetic products. However, compatibility thereof with cyanoacrylate systems is not described at all in literature. By contrast, the present inventor has unexpectedly found that such compounds can be employed in cyanoacrylate compositions as a non-hazardous free radical stabilizer.

The curable cyanoacrylate composition according to the present invention may comprise the at least one free radical stabilizer of formula (I) in an amount of e.g. 0.1 to 5.0 weight %, based on the total weight of the curable cyanoacrylate composition. In a preferred embodiment, the curable cyanoacrylate composition comprises the at least one free radical stabilizer(s) of formula (I) in an amount of 0.2 to 4.0 weight %, more preferably 0.3 to 3.0 weight %, based on the total weight of the curable cyanoacrylate composition.

The curable cyanoacrylate composition according to the present invention naturally further comprises at least one cyanoacrylate monomer. Suitable cyanoacrylate monomers are well-known in the art. The present invention is not limited to a particular type of cyanoacrylate monomer. For example, the cyanoacrylate monomer may be selected from at least one compound of the formula $R^7HC=C(CN)—COOR^8$, wherein $R^7$ is hydrogen, linear or branched $C_1$-$C_{15}$ alkyl, linear or branched $C_2$-$C_{15}$ alkenyl, linear or branched $C_2$-$C_{15}$ alkynyl, linear or branched $C_2$-$C_{15}$ alkoxy, cycloalkyl, aralkyl, allyl or aryl, wherein $R^7$ optionally may be further substituted with at least one halogen and/or at least one $C_1$-$C_{15}$ alkoxy group; and $R^8$ is hydrogen, linear or branched $C_1$-$C_{15}$ alkyl, linear or branched $C_2$-$C_{15}$ alkenyl, linear or branched $C_2$-$C_{15}$ alkynyl, linear or branched $C_2$-$C_{15}$ alkoxy, cycloalkyl, aralkyl or aryl, wherein $R^8$ optionally may be further substituted with at least one halogen and/or at least one $C_1$-$C_{15}$ alkoxy group.

In a preferred embodiment, the at least one cyanoacrylate monomer is selected from methyl cyanoacrylate, ethyl cyanoacrylate, propyl cyanoacrylates, butyl cyanoacrylates, octyl cyanoacrylates, allyl cyanoacrylate, β-methoxyethyl cyanoacrylate, β-ethoxyethyl cyanoacrylate and combinations thereof. A particularly desirable one is ethyl cyanoacrylate.

The amount of cyanoacrylate monomer in the curable cyanoacrylate composition according to the present invention is not particularly limited. For example, the curable cyanoacrylate composition may comprise the at least one cyanoacrylate monomer in an amount of at least 50 weight %, based on the total weight of the curable cyanoacrylate composition. In a preferred embodiment, the curable cyanoacrylate composition comprises the at least one cyanoacrylate monomer in an amount of 60.0 to 99.9 weight %, based on the total weight of the curable cyanoacrylate composition. Preferably, the curable cyanoacrylate composition comprises the at least one cyanoacrylate monomer in an amount of 88.0 to 99.8 weight %, more preferably 97.0 to 99.5 weight %, based on the total weight of the curable cyanoacrylate composition.

As known in the art, cyanoacrylates also can undergo anionic polymerization. Therefore, cyanoacrylate compositions typically further comprise an anionic stabilizer (also known as "acid stabilizer") to prevent anionic polymerization. The anionic stabilizer is usually selected from a Lewis acid or a Brønsted acid. Thus, the curable cyanoacrylate composition according to the present invention normally further comprises a Lewis acid or a Brønsted acid as an anionic stabilizer. The anionic stabilizer is preferably selected from boron trifluoride ($BF_3$) and its complexes, sulfur dioxide ($SO_2$), or hydrogen fluoride (HF). The anionic stabilizer may be comprised in the curable cyanoacrylate composition in an amount of e.g. 0.0005 to 5.0 weight %, based on the total weight of the curable cyanoacrylate composition.

Cyanoacrylate compositions may further contain additional additives as well-known in the art. For example, the curable cyanoacrylate composition according to the present invention may also include usual additives selected from e.g. thickeners, thixotroping agents, accelerators, retarders, plasticizers, adhesion promoters, pigments or dyes. A person skilled in the art will be readily able to select suitable additives and the amounts thereof as needed. For example, additional additives conventionally employed in cyanoacrylate compositions may be present in the curable cyanoacrylate composition according to the present invention in an amount of up to 60 weight %, based on the total weight of the curable cyanoacrylate composition. In view of performance, such conventional additives are present in the curable cyanoacrylate composition according to the invention in an amount of preferably up to only 45 weight %, more preferably up to 30 weight %, based on the total weight of the curable cyanoacrylate composition.

The present invention is also suitable to stabilize photocurable cyanoacrylate compositions, such as UV-curable cyanoacrylate compositions against free radical polymerization. Photocurable cyanoacrylate compositions are known in the art, and are described e.g. in U.S. Pat. No. 5,922,783 or WO 2020/206405. Photocurable cyanoacrylate compositions typically comprise a metallocene compound and a photoinitiator, as known by a person skilled in the art. Thus, in one embodiment, the present invention relates to a curable cyanoacrylate composition as described above further comprising a metallocene compound and a photoinitiator. A person skilled in the art will be able to select suitable metallocene compounds or photoinitiators and the amounts thereof e.g. by reference to U.S. Pat. No. 5,922,783 or WO 2020/206405.

The curable cyanoacrylate compositions according to the present invention can be employed in any field where cyanoacrylate adhesives are typically used. Examples thereof include but are not limited to industrial manufacture or household use. The present invention using a non-hazardous free radical stabilizer is especially advantageous in fields where the cyanoacrylate adhesive come into contact with humans, e.g. in the field of toy manufacture, the manufacture of containers for food or beverages, or in the field of cosmetics, for example for cosmetic packaging or for articles that bond to skin e.g. bonding false lashes, as well as in the medical field, for example as a liquid plaster, etc.

The present invention also relates to the use of a compound of formula (I) as defined above for inhibiting free radical polymerization in a composition comprising at least one cyanoacrylate monomer. Alternatively, the present invention relates to a method of inhibiting free radical polymerization in a composition comprising at least one cyanoacrylate monomer, the method comprising the step of adding at least one compound of formula (I) to the composition. Preferred embodiments of the use (or method) according to the present invention as regards e.g. preferred compounds of formula (I) or preferred cyanoacrylate monomers as well as the amounts thereof, respectively, are already described above in connection with embodiments relating to the inventive curable cyanoacrylate composition.

The present invention is further illustrated by means of the following examples.

EXAMPLES

Materials:
Cyanoacrylate monomer: Ethyl cyanoacrylate
Free radical stabilizers:
Comparative: Hydroquinone (HQ), butylated hydroxyanisole (BHA)
According to invention: Oxynex® ST (designated O.ST in Table 1 below) or RonaCare® AP (designated R.AP in Table 1), both available from Merck KGaA (Germany)

Cyanoacrylate monomer (CA) was purified by vacuum distillation directly from the production vessel. Certain quantities needed for testing were redirected into a separate container. Immediately after taking off the container from the distillation line a quantity of 5 ppm acid stabilizer ($BF_3$-complex) was added to prevent immediate polymerization. The level of purity was checked using GC-MS and HPLC. An amount of >99.5% cyanoacrylate monomer and especially no hydroquinone (HQ) was detected in the sample quantities further used.

In a second step, portions of the pre-stabilized cyanoacrylate were taken off and free radical stabilizer was added to achieve the concentrations listed in Table 1 below. Samples including poly(methyl methacrylate) (PMMA) as a thickener have been prepared likewise.

TABLE 1

| Sample Compositions in [weight %] | | | | | |
|---|---|---|---|---|---|
| | CA | HQ | BHA | O.ST | R.AP | PMMA |
| CE1 | 99.0 | 1 | | | | |
| CE2 | 99.0 | | 1 | | | |
| IE1 | 97.5 | | | 2.5 | | |
| IE2 | 97.5 | | | | 2.5 | |
| IE3 | 99.0 | | | 1 | | |
| IE4 | 99.0 | | | | 1 | |
| IE5 | 99.5 | | | 0.5 | | |
| IE6 | 99.5 | | | | 0.5 | |
| IE7 | 94.5 | | | 0.5 | | 5 |
| IE8 | 94.5 | | | | 0.5 | 5 |

Comparative example 1 (CE1) and comparative example 2 (CE2) use conventional free radical stabilizers already known for use with cyanoacrylates. Inventive examples 1 to 8 (IE1 to IE8) employ non-hazardous free radical stabilizers selected in accordance with the present invention.

The viscosities of the sample compositions were determined at +20° C. and 160 rpm using a cone-plate rheometer (in compliance with documentation standards according to ISO 9001 or IATF 16949). Table 2 below shows the average results of three measurements, respectively.

The term "14 d, 60° C." in Table 2 indicates that the liquid adhesive sample was aged for 14 days at +60° C. (prior to preparation of test specimen including a substrate as described further below).

The term "360 d, 22° C." indicates that the liquid adhesive sample was aged for one year at ambient temperature.

TABLE 2

| Average viscosities of fresh and aged sample compositions in [mPa · s] | | | |
|---|---|---|---|
| | initial | 14 d, 60° C. | 360 d, 22° C. |
| CE1 | 2 | 2 | 3 |
| CE2 | 2 | 5 | 7 |
| IE1 | 3 | 3 | 3 |
| IE2 | 3 | 3 | 3 |
| IE3 | 2 | 3 | 2 |
| IE4 | 2 | 3 | 3 |
| IE5 | 2 | 4 | 4 |
| IE6 | 2 | 5 | 4 |
| IE7 | 463 | 489 | 510 |
| IE8 | 455 | 512 | 533 |

As can be seen from Table 2 above, the non-hazardous free radical stabilizers employed according to the invention show good compatibility to cyanoacrylate monomers and are effective to prevent polymerization on a similar level as conventional "toxic" free radical stabilizers so far used in the field. This even applies in the presence of additives typically used in the cyanoacrylate field, such as thickeners as can be seen from inventive examples 1E7 and 1E8.

Reactivity of the sample compositions was tested by bonding EPDM rubber profile surfaces to each other using the sample compositions as an adhesive. The average set times obtained when tested five times, respectively, are listed in Table 3 below.

TABLE 3

| Set time on EPDM in [s] | | | |
|---|---|---|---|
| | initial | 14 d, 60° C. | 360 d, 22° C. |
| CE1 | 1 | 1 | 1 |
| CE2 | 1 | 2 | 2 |

TABLE 3-continued

| | Set time on EPDM in [s] | | |
|---|---|---|---|
| | initial | 14 d, 60° C. | 360 d, 22° C. |
| IE1 | 7 | 8 | 7 |
| IE2 | 8 | 10 | 9 |
| IE3 | 2 | 2 | 2 |
| IE4 | 2 | 2 | 3 |
| IE5 | 1 | 1 | 1 |
| IE6 | 1 | 1 | 2 |
| IE7 | 2 | 3 | 3 |
| IE8 | 2 | 3 | 3 |

As can be seen from Table 3 above, the non-hazardous free radical stabilizer selected in accordance with the present invention does not substantially impair reactivity of the obtained cyanoacrylate compositions. Rather, reactivity is at an acceptable level in the same range as in the presence of conventional free radical stabilizers.

The mechanical strength obtained with the sample compositions was tested by bonding surface-cleaned steel specimen without further pre-treatment (along the lines of DIN EN 1465). Average data resulting from three tests, respectively, are shown in Table 4 below.

TABLE 4

| Average shear-strength test results on steel specimen in [N mm$^{-2}$] | | |
|---|---|---|
| | initial | 14 d, 60° C. |
| CE1 | 22 | 21 |
| CE2 | 18 | 16 |
| IE5 | 21 | 20 |
| IE6 | 21 | 18 |
| IE7 | 20 | 21 |
| IE8 | 19 | 20 |

Mechanical strength of the adhesive bond resulting in the presence of non-hazardous free radical stabilizers selected in accordance with the present invention is not impaired.

It was unexpectedly found that conventional free radical stabilizers can be replaced by non-hazardous free radical stabilizers selected in accordance with the present invention. The non-hazardous free radical stabilizers selected in accordance with the present invention can well be formulated into cyanoacrylates. The sample compositions achieve similar properties in e.g. shelf-life as well as adhesive properties compared to state-of-art compositions containing hazardous stabilizers such as HQ or BHA.

What is claimed:

1. A curable cyanoacrylate composition comprising
   (i) at least one cyanoacrylate monomer, and
   (ii) at least one free radical stabilizer,
   wherein the free radical stabilizer comprises one or more compound(s) of formula (I)

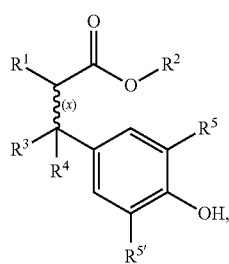

(I)

wherein (x) denotes either a double bond and $R^3$ is absent, or (x) denotes a single bond and $R^3$ is hydrogen, linear $C_1$-$C_8$ alkyl, branched or cyclic $C_3$-$C_8$ alkyl, linear $C_1$-$C_8$ alkoxy, branched or cyclic $C_3$-$C_8$ alkoxy, linear $C_2$-$C_8$ alkenyl, or branched or cyclic $C_3$-$C_8$ alkenyl;

$R^1$ is hydrogen, linear $C_1$-$C_8$ alkyl, branched or cyclic $C_3$-$C_8$ alkyl, linear $C_1$-$C_8$ alkoxy, branched or cyclic $C_3$-$C_8$ alkoxy, linear $C_2$-$C_8$ alkenyl, branched or cyclic alkenyl, or a group —C(O)—O—$R^{2'}$, wherein is linear $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl, which linear $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl optionally may be interrupted by one or more oxygen atoms;

$R^2$ is linear $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl, which linear $C_1$-$C_{12}$ alkyl, branched or cyclic $C_3$-$C_{12}$ alkyl, linear $C_2$-$C_{12}$ alkenyl, or branched or cyclic $C_3$-$C_{12}$ alkenyl optionally, may be interrupted by one or more oxygen atoms;

$R^4$ is hydrogen, linear $C_1$-$C_8$ alkyl, branched or cyclic $C_3$-$C_8$ alkyl, linear $C_1$-$C_8$ alkoxy, branched or cyclic $C_3$-$C_8$ alkoxy, linear $C_2$-$C_8$ alkenyl, or branched or cyclic $C_3$-$C_8$ alkenyl; and $R^5$ and $R^{5'}$ independently are hydrogen or a group —O—$R^6$, wherein $R^6$ independently is hydrogen, linear $C_1$-$C_8$ alkyl, branched or cyclic $C_3$-$C_8$ alkyl, linear $C_2$-$C_8$ alkenyl, or branched or cyclic $C_3$-$C_8$ alkenyl, wherein one of $R^3$ or $R^4$ together with $R^1$ may form a 5- to 18-membered saturated or unsaturated ring together with the carbon atoms to which they are attached, which is optionally interrupted by one or more oxygen atoms; or $R^3$ and $R^4$ may form a 5- to 18-membered saturated or unsaturated ring together with the carbon atom to which they are attached which is optionally interrupted by one or more oxygen atoms; or $R^1$ with $R^3$ and $R^4$ together with the carbon atoms to which they are attached may form a 5- to 12-membered saturated or unsaturated bicyclic ring, which is optionally interrupted by one or more oxygen atoms.

2. The curable cyanoacrylate composition according to claim 1, wherein in the formula (I)

$R^1$ is a group —C(O)—O—$R^{2'}$, wherein $R^{2'}$ is branched or cyclic $C_3$-$C_{12}$ alkyl, which is optionally interrupted by one or two oxygen atoms;

$R^2$ is branched or cyclic $C_3$-$C_{12}$ alkyl, which is optionally interrupted by one or two oxygen atoms;

$R_3$ is hydrogen, linear $C_1$-$C_4$ alkyl, or branched $C_3$-$C_4$ alkyl in case (x) denotes a single bond; and is absent when (x) denotes a double bond $R^4$ is hydrogen, linear $C_1$-$C_4$ alkyl, or branched $C_3$-$C_4$ alkyl; and $R^5$ and $R^{5'}$ independently are hydrogen or a group —O—$R^6$, wherein $R^6$ independently is hydrogen, linear $C_1$-$C_4$ alkyl, or branched $C_3$-$C_4$ alkyl, wherein $R^3$ and $R^4$ may form a 5- or 6-membered ring together with the carbon atom to which they are attached which is optionally interrupted by one or two oxygen atoms.

3. The curable cyanoacrylate composition according to claim 2, wherein in the formula (I)

$R^1$ is a group —C(O)—O—$R^{2'}$, wherein $R^{2'}$ is branched $C_6$-$C_{10}$ alkyl;

$R^2$ is branched $C_6$-$C_{10}$ $R^3$ is hydrogen or methyl in case (x) denotes a sing bond; and is absent when (x) denotes a double bond;

$R^4$ is hydrogen or methyl; and.

$R^5$ and independently are —O—$CH_3$ or —$OCH_2CH_3$.

4. The curable cyanoacrylate composition according to claim 3, wherein in the formula (I)

$R^3$ is hydrogen in case (x) denotes a covalent single bond; and is absent when (x) denotes a covalent double bond;

$R^4$ is hydrogen; and $R^5$ and $R^{5'}$ are —O—$CH_3$.

5. The curable cyanoacrylate composition according to claim 1, wherein the cyanoacrylate monomer is selected from at least one compound of the formula $R^7HC=C(CN)—COOR^8$, wherein $R^7$ is hydrogen, linear or branched $C_1$-$C_{15}$ alkyl, linear or branched $C_2$-$C_{15}$ alkenyl, linear or branched $C_2$-$C_{15}$ alkenyl, linear or branched $C_2$-$C_{15}$ alkoxy, cycloalkyl, aralkyl, allyl or aryl, wherein $R^7$ optionally may be further substituted with at least one halogen and/or at least one $C_1$-$C_{15}$ alkoxy group; and $R^8$ is hydrogen, linear or branched $C_1$-$C_{15}$ is alkyl, linear or branched $C_2$-$C_{15}$ alkenyl, linear or branched $C_2$-$C_{15}$ alkynyl, linear or branched $C_2$-$C_{15}$ alkoxy, cycloalkyl, aralkyl or aryl, wherein $R^8$ optionally may be further substituted with at least one halogen and/or at least one $C_1$-$C_{15}$ alkoxy group; and wherein the cyanoacrylate monomer is selected from the group consisting of methyl cyanoacrylate, ethyl cyanoacrylate, propyl cyanoacrylates, butyl cyanoacrylates, octyl cyanoacrylates, allyl cyanoacrylate, β-methoxyethyl cyanoacrylate, β-ethoxyethyl cyanoacrylate and combinations thereof.

6. The curable cyanoacrylate composition according to claim 1, wherein the composition comprises the at least one free radical stabilizer in an amount of 0.1 to 5.0 weight %, based on the total weight of the curable cyanoacrylate composition.

7. The curable cyanoacrylate composition according to claim 1, wherein the composition comprises the at least one cyanoacrylate monomer in an amount of 60.0 to 99.9 weight %, based on the total weight of the curable cyanoacrylate composition.

8. The curable cyanoacrylate composition according to claim 1 further comprising an anionic stabilizer, wherein the anionic stabilizer is a Lewis acid or a Brønsted acid and is selected from the group consisting of boron trifluoride ($BF_3$) and its complexes, sulfur dioxide ($SO_2$), or hydrogen fluoride (HF).

9. The curable cyanoacrylate composition according to claim 8, wherein the composition comprises the anionic stabilizer in an amount of 0.0005 to 5.0 weight %, based on the total weight of the curable cyanoacrylate composition.

10. The curable cyanoacrylate composition according to claim 1 further comprising additional additives selected from the group consisting of thickeners, thixotroping agents, accelerators, retarders, plasticizers, adhesion promoters, pigments or dyes.

11. The curable cyanoacrylate composition according to claim 10, wherein the additional additives are present in an amount of up to 60 weight %, based on the total weight of the curable cyanoacrylate composition.

12. The curable cyanoacrylate composition according to claim 1 further comprising a metallocene compound, and a photoinitiator.

13. The curable cyanoacrylate composition of claim 1 comprising:

from 88.0 to 99.8% by weight of the cyanoacrylate monomer, and from 0.2 to 4.0% by weight of the free radical stabilizer.

14. The curable cyanoacrylate composition of claim 1 comprising:

from 97.0 to 99.5% by weight of the cyanoacrylate monomer, and from 0.3 to 3.0% by weight of the free radical stabilizer.

15. The curable cyanoacrylate composition of claim 13 further comprising an anionic stabilizer.

16. An article comprising the curable cyanoacrylate composition of claim 1.

17. The article of claim 16 selected from the group consisting of food container, beverage container, cosmetic packaging, and articles that bond to skin.

* * * * *